United States Patent [19]

Goettsche et al.

[11] Patent Number: 4,857,322

[45] Date of Patent: Aug. 15, 1989

[54] WOOD PRESERVATIVE

[75] Inventors: Reimer Goettsche, Baden-Baden; Hans-Norbert Marx, Buehl-Weitenung; Wendelin Hettler, Sinzheim-Muellhofen, all of Fed. Rep. of Germany

[73] Assignee: Dr. Wolman GmbH, Sinzheim, Fed. Rep. of Germany

[21] Appl. No.: 118,011

[22] Filed: Nov. 9, 1987

[30] Foreign Application Priority Data

Nov. 14, 1986 [DE] Fed. Rep. of Germany ....... 3639063

[51] Int. Cl.$^4$ ...................... A01N 59/20; A01N 55/02
[52] U.S. Cl. ..................... 424/633; 514/184; 514/499; 514/500; 424/632; 424/634; 424/637; 424/638
[58] Field of Search ................ 424/78, 140, 141, 143; 514/184, 499, 500

[56] References Cited

U.S. PATENT DOCUMENTS

| | | | |
|---|---|---|---|
| 4,001,400 | 1/1977 | Hager | 424/134 |
| 4,048,324 | 9/1977 | Kohn | 424/294 |
| 4,193,993 | 3/1980 | Hilditch | 514/500 |
| 4,737,491 | 4/1988 | Leppävuori et al. | 514/184 |

FOREIGN PATENT DOCUMENTS

| | | |
|---|---|---|
| 519146 | 11/1981 | Australia . |
| 0039538 | 11/1981 | European Pat. Off. . |
| 0136137 | 4/1985 | European Pat. Off. . |
| 3522000 | 6/1985 | Fed. Rep. of Germany . |
| 8203817 | 11/1982 | World Int. Prop. O. . |

Primary Examiner—Paul Lieberman
Assistant Examiner—Willie J. Thompson
Attorney, Agent, or Firm—Oblon, Fisher, Spivak, McClelland & Maier

[57] ABSTRACT

Wood preservatives based on a copper compound and an aliphatic carboxylic acid and additionally containing a polyamine, and a method for preserving wood with these preservatives.

14 Claims, No Drawings

WOOD PRESERVATIVE

The present invention relates to a wood preservative, for example in the form of an aqueous solution, which contains a copper compound, an aliphatic carboxylic acid and a polyamine.

Wood preservatives based on alkanolamines, copper compounds and aliphatic $C_6$–$C_{18}$-monocarboxylic acids are known (Australian Pat. No. 519,146). When wood is impregnated by large-scale industrial processes, for example the pressure impregnation process, with aqueous solutions of this wood preservative, the depth of penetration and the distribution of the copper carboxylates which form in the wood are not sufficient to ensure preservation of the wood, for example in the case of round woods, such as poles or palisades, in particular when they are used in permanent contact with the ground. For example, a depth of penetration of copper of only about 10 mm has been achieved.

We have found that the abovementioned disadvantages do not occur in wood preservatives based on copper compounds, aliphatic carboxylic acids and polyamines. Examples of particularly suitable polyamines in this case are aliphatic polyamines, alkylenepolyamines of 3 to 9 carbon atoms and 2 to 4 nitrogen atoms, 1,3-diaminopropane, 1-methylamino-3-aminopropane, dipropylenetriamine (3,3'-diaminodipropylamine) and tripropylenetetramine. 1,3-diaminopropane is preferred.

Examples of suitable aliphatic carboxylic acids are $C_5$–$C_{20}$-monocarboxylic acids, such as hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid, isodecanoic acid and Versatic acids (highly branched monocarboxylic acids), and $C_5$–$C_{20}$-dicarboxylic acids, eg. decanedicarboxylic acid. Polycarboxylic acids, such as polyacrylic acids, are also suitable. 2-ethylhexanoic acid is preferred.

These acids react with copper to form water-insoluble salts, which are dissolved in the alkaline medium as a result of the complex-forming action of the abovementioned amines.

Suitable copper compounds are water-soluble or insoluble compounds (eg. copper salts, such as copper sulfate, copper hydroxide, copper carbonate, copper acetate, copper borate, copper fluoride and copper fluoborate). Copper carbonate is preferred.

Some of the copper can, for example, also be replaced by an appropriate zinc compound.

In concentrated form, the water-dilutable agents contain the copper, calculated as the element, in an amount of from 1 to 15% by weight.

Additional anions capable of diffusion, eg. borates, fluorides or borofluorides, may be present; after impregnation of the wood, these anions diffuse and thus protect regions inaccessible to an impregnation, such as the heartwood.

The action of the wood preservative can be supplemented, for example, by salts of N-cyclohexyldihydroxydiazenium oxide, for example the copper salt or the potassium salt. Combination with quaternary ammonium compounds is also suitable for this purpose.

An example of a quaternary ammonium compound is a compound of the general formula $(R^1R^2R^3R^4N)^+Z^-$, where $R^1$ is alkyl of 8 to 20, in particular 12 to 20, carbon atoms, or benzyl which is unsubstituted or substituted by $C_1$–$C_{20}$-alkyl or halogen, $R^2$ is $C_1$–$C_6$-alkyl or $C_3$–$C_{19}$-alkoxyalkyl, $R^3$ is $C_1$–$C_6$-alkyl or $C_1$–$C_4$-alkoxy and $R^4$ is $C_1$–$C_{20}$-alkyl, or two radicals $R^1$ to $R^4$, together with the nitrogen atom, form a heterocyclic radical which contains four or five atoms, one or two nitrogen atoms and one, two or three double bonds, the carbon atoms being unsubstituted or substituted by $C_1$–$C_4$-alkyl or halogen, and Z is an acid radical.

Suitable concentrates contain, for example,
5–40% of a copper compound,
10–40% of a carboxylic acid/polycarboxylic acid,
5–40% of a polyamine,
up to 40% of a fungicidal anion capable of diffusion,
up to 75% of a quaternary ammonium salt and
up to 30% of a salt of N-cyclohexyldihydroxydiazenium oxide,
the sum being 100 (% by weight) in each case.

If necessary, minor amounts of other components, such as other amines, ammonia, wetting agents, water softeners (nitriloacetic acid, etc.) and, if required, water may be present, the amounts of the latter however being kept small where possible and essentially serving to facilitate handling.

However, the invention also relates to the impregnation solutions obtainable by dilution of the concentrates with water, in accordance with the required concentrations for use and depending on the impregnation method and the degree of danger to the wood.

The concentrates, which may be in the form of pastes or viscous solutions (if appropriate, also in the form of a solid salt), are most readily prepared by initially taking a polyamine, with or without water, and dissolving the carboxylic acids and, where relevant, the salts containing fungicidal anions and/or salts of N-cyclohexyldihydroxydiazenium oxide therein. The copper compounds then dissolve in this mixture with complex formation. The alkalinity of the concentrates is adjusted, on the one hand, to ensure that sufficient polyamine is present to dissolve the copper compound and, on the other hand, by adding, for example, further polyamines, amines or alkali metal hydroxides to bring the pH of the dilute solutions for use to, in general, above 8, in particular from 8.5 to 10 (concentration-dependent). When impregnation is carried out, the copper compound penetrates thoroughly into the wood, the major part of the copper (about 70–95%) being fixed in the wood.

During impregnation, the wood preservatives penetrate the wood thoroughly, and the impregnatable regions of the wood (for example sapwood in pine) are entirely impregnated in the pressure impregnation process. Furthermore, penetration of water into the impregnated wood is more difficult, and the impregnated wood thus becomes more highly water-repellent.

To determine the depth of penetration, pine palisades having a length of 1.20 m, a diameter of 15–20 cm and a sapwood width of more than 30 mm were impregnated by the pressure impregnation method (1 hour under reduced pressure, 2 hours under superatmospheric pressure). To determine the depth of penetration of copper, the impregnated woods were cut open in the middle, the cut surface was treated with diethyl dithiocarbamate/Na salt solution (brown coloration with copper) and the depth of penetration of the copper was measured. 2 palisades were impregnated per test.

KNOWN COMPARATIVE EXAMPLES

| Wood preservative I | | |
|---|---|---|
| | 13.3% | Copper carbonate |
| | 30.0% | Ethanolamine |
| | 5.0% | Boric acid |
| | 36.7% | 2-ethylhexanoic acid |
| | 15.0% | Water |
| | 100% | |
| Concentration for use: | 4% | |

The following mean penetration depths were determined: 13.7 mm and 12.0 mm

| Wood preservative II | | |
|---|---|---|
| | 13.3% | Copper carbonate |
| | 30.0% | Ethanolamine |
| | 36.7% | Polyacrylic acid (n = 10–100) |
| | 20.0% | Water |
| | 100% | |
| Concentration for use: | 4% | |

Mean penetration depths: 9.1 mm and 14.0 mm

Examples according to the invention

| Example 1 | | |
|---|---|---|
| | 13.3% | Copper carbonate |
| | 28.0% | Dipropylenetriamine |
| | 10.0% | Boric acid |
| | 42.0% | Nonanoic acid |
| | 6.7% | Water |
| | 100% | |
| Concentration for use: | 4% | |

Mean penetration depths: 32.1 mm and 29.3 mm

| Example 2 | | |
|---|---|---|
| | 13.3% | Copper carbonate |
| | 28.0% | Dipropylenetriamine |
| | 10.0% | Boric acid |
| | 36.7% | Isooctanoic acid |
| | 12.0% | Water |
| | 100% | |
| Concentration for use: | 4% | |

Mean penetration depths: 41.0 mm and 34.1 mm

| Example 3 | | |
|---|---|---|
| | 10.0% | Copper carbonate |
| | 16.5% | 1,3-diaminopropane |
| | 27.5% | 2-ethylhexanoic acid |
| | 4.0% | Boric acid |
| | 2.5% | Nitrilotriacetic acid |
| | 5.0% | Potassium salt of N—cyclohexyldihydroxy-diazenium oxide |
| | 34.5% | Water |
| | 100% | |
| Concentration for use: | 4% | |

Mean penetration depths: 29.1 mm and 37.2 mm

| Example 4 | | |
|---|---|---|
| | 13.3% | Copper carbonate |
| | 13.3% | 1,3-diaminopropane |
| | 11.4% | 1-methylamino-3-amino-propane |
| | 10.0% | Boric acid |
| | 36.7% | 2-ethylhexanoic acid |
| | 15.3% | Water |
| | 100% | |
| Concentration for use: | 4% | |

Mean penetration depths: 36.5 mm and 28.3 mm

| Example 5 | | |
|---|---|---|
| | 10.0% | Copper carbonate |
| | 15.0% | Tripropylenetetramine |
| | 10.0% | Dipropylenetriamine |
| | 25.0% | 2-ethylhexanoic acid |
| | 20.0% | Dimethyl—$C_{12}$—alkylbenzyl-ammonium chloride |
| | 20.0% | Water |
| | 100% | |
| Concentration for use: | 4% | |

The following mean penetration depths were determined: 35.2 mm and 40.1 mm

Furthermore, pine sapwood blocks were impregnated with novel solutions and stored for about 6 weeks for fixing and drying (water content 16–18%).

The water absorption of the impregnated blocks as a result of further impregnation with water was determined by weight and compared with that of blocks which had been treated exclusively with water and correspondingly dried. The further water absorption of these blocks (blank test) was set at 100 for purposes of comparison. The measurements were carried out using 10 blocks in each case. It was found that the impregnated blocks absorbed less water than the blocks treated with water.

We claim:

1. A wood preservative, comprising:
   (a) about 5–40 wt.% of a copper compound,
   (b) about 10–40 wt.% of an aliphatic monocarboxylic acid, aliphatic dicarboxylic acid or polycarboxylic acid, or a mixture thereof, and
   (c) about 5–40 wt.% of a polyamine containing 3–9 carbon atoms, 2–4 nitrogen atoms and containing at least one primary amino group, based upon the total weight of the mixture.

2. The preservative as claimed in claim 1, wherein the monocarboxylic acid is 2-ethylhexanoic acid.

3. The preservative as claimed in claim 1, wherein the monocarboxylic acid is an isooctanoic acid.

4. The preservative as claimed in claim 1, wherein the copper compound is copper oxide, copper hydroxide or copper carbonate.

5. The preservative as claimed in claim 1, wherein the polyamine is 1,3-diaminopropane.

6. The preservative as claimed in claim 1, which additionally contains an alkali metal salt or a copper salt of N-cyclohexyldihydroxydiazenium oxide.

7. A method of protecting wood, which comprises treating the wood with an impregnation solution comprising an aqueous solution containing an effective amount of the wood preservative of claim 1.

8. The preservative as claimed in claim 1, wherein said monocarboxylic acid is a $C_5$–$C_{20}$-monocarboxylic acid.

9. The preservative as claimed in claim 1, wherein said dicarboxylic acid is a $C_5$–$C_{20}$-dicarboxylic acid.

10. The preservative as claimed in claim 1, wherein said polycarboxylic acid is polyacrylic acid.

11. The preservative as claimed in claim 1, wherein said copper compound is selected from the group consisting of copper sulfate, copper hydroxide, copper carbonate, copper acetate, copper borate, copper fluoride and copper fluoborate.

12. The preservative as claimed in claim 1, which has a pH of at least 8.0.

13. The preservative as claimed in claim 12, which has a pH in the range of 8.5 to 10.

14. The method as claimed in claim 7, wherein said treatment comprises subjecting said wood to said wood preservative using the pressure impregnation method.

* * * * *